(12) United States Patent
Mercader Badia et al.

(10) Patent No.: US 7,691,600 B2
(45) Date of Patent: Apr. 6, 2010

(54) METHOD FOR DETECTING AND/OR IDENTIFYING BACTERIA PRESENT IN A SAMPLE

(75) Inventors: Josep Vicent Mercader Badia, Lyons (FR); Bruno Colin, Marcy l'Etoile (FR); Vincent Atrache, Caluire (FR)

(73) Assignee: Biomerieux, Marcy l'Etoile (FR)

( * ) Notice: Subject to any disclaimer, the term of this patent is extended or adjusted under 35 U.S.C. 154(b) by 379 days.

(21) Appl. No.: 10/551,989

(22) PCT Filed: Apr. 2, 2004

(86) PCT No.: PCT/FR2004/050140

§ 371 (c)(1),
(2), (4) Date: Oct. 4, 2005

(87) PCT Pub. No.: WO2004/092401

PCT Pub. Date: Oct. 28, 2004

(65) Prior Publication Data

US 2007/0020720 A1 Jan. 25, 2007

(30) Foreign Application Priority Data

Apr. 7, 2003 (FR) .................................... 0304262

(51) Int. Cl.
*G01N 27/447* (2006.01)
(52) U.S. Cl. ........................... 435/34; 436/809; 204/274
(58) Field of Classification Search ....................... None
See application file for complete search history.

(56) References Cited

U.S. PATENT DOCUMENTS

| 4,563,418 A | | 1/1986 | Ward, Jr. |
| 5,132,229 A | | 7/1992 | Ward, Jr. |
| 5,624,815 A | * | 4/1997 | Grant et al. .................... 435/30 |
| 6,605,475 B1 | * | 8/2003 | Taylor et al. ................. 436/180 |

FOREIGN PATENT DOCUMENTS

| DE | 196 05 753 A1 | 9/1997 |
| EP | 0 259 116 A2 | 3/1988 |
| WO | WO 00/63668 | 10/2000 |

* cited by examiner

*Primary Examiner*—Lisa J Hobbs
(74) *Attorney, Agent, or Firm*—Oliff & Berridge, PLC (57) ABSTRACT

The present invention relates to a method for detecting and/or identifying bacteria present in a liquid or solid sample, characterized in that:
 a. the sample that may contain said bacteria is placed in a liquid culture medium, in a first container,
 b. a second container comprising at least one system for detecting said bacteria is provided,
 c. a means of transfer between the first container and the second container is provided,
 d. a temperature T1 is applied inside the second container, then
 e. a temperature T2 is applied inside the second container,
 f. the temperature T1 is higher than the temperature T2 such that a defined volume of culture medium is transferred from the first container to the second container,
 g. the presence or absence of bacteria is determined and/or the bacteria are identified within the detection system.

6 Claims, 5 Drawing Sheets

METHOD FOR DETECTING AND/OR IDENTIFYING BACTERIA PRESENT IN A SAMPLE

The present invention relates to a method for detecting and/or identifying bacteria present in a liquid or solid sample. The invention also relates to a device for detecting and/or identifying bacteria present in such a sample.

The identification of bacteria in foods is essential for public health. For example, bacteria of the *Salmonella* genus, which can be found in a large number of foods, are the cause of many pathologies in humans (typhoid fever, food poisoning). Similarly, the isolation and identification of the *Listeria* bacterium is a major obligation of the monitoring of agrofoods hygiene and of medical bacteriology. Thus, among the bacteria of the *Listeria* genus, the *Listeria monocytogenes* species, known to be pathogenic for humans, can cause listeriosis, which is sometimes lethal (25 to 30% of cases) in immunodepressed individuals and young children. It is therefore very important to provide a reliable and rapid test for detecting contaminations with these bacteria, which test must be both sensitive and specific. Finally, the identification of bacteria of the *Staphylococcus* genus is also essential. Most of these species are opportunistic pathogens in humans at high risk in the event of a skin injury due to a trauma or due to direct implantation of a medical product. Moreover, the *Staphylococcus aureus* species is a bacterium that is often found in patients who have to receive hospital care involving devices such as syringes or catheters. There is therefore a great advantage in detecting the presence of this pathogenic bacterium that is increasingly involved in nosocomial diseases.

Many tests for detecting bacteria currently exist. In general, these detection tests require a pre-enrichment comprising:
- a restoring step, allowing the bacteria to recover from the stress induced by the culturing, and
- a bacterial exponential growth step, which is essential when few bacteria are initially present in the sample, and
- a step for detecting the bacteria, which should preferably be carried out at the bacterial growth peak and before the appearance of the bacterial death phase, which is observed in any bacterial culture.

By way of indication of a method for detecting bacteria, mention may be made of the method for detecting *Salmonella* described in patent U.S. Pat. No. 4,563,418, which is based on an immunoprecipitation. The detection of these bacteria is carried out, after the pre-enrichment and bacterial growth step, after migration in a culture medium pre-enriched with *Salmonella* and reaction with antibodies directed against *Salmonella*. Mention may also be made of a comparable method, also based on an immunoprecipitation, which is given in patent U.S. Pat. No. 5,132,229. In these methods, the user must, however, manually carry out a step consisting in transferring the culture medium, pre-enriched with bacteria, to the migration gel, which can induce problems, in particular of contamination, but also risks for the handler's health.

Mention may also be made of more recent methods, based mainly on migration of the bacteria through a medium selective for the bacterial species that it is specifically desired to detect. Thus, patent application EP-A-0.259.116 provides a method for detecting the presence of *Salmonella* in a sample, the method comprising the migration of the *Salmonella* present in a pre-enriched culture medium to a selective medium specific for *salmonella*. The *salmonellae* then migrate to the detection system, allowing them to be detected, whereas the other bacteria that may be present in the sample are stopped by the selective medium. However, in this method, the culture medium remains in contact with the selective medium and the detection system, which constitutes the major problem of this type of method. Thus, if the sample is highly contaminated, the bacteria other than the *salmonellae* present in the culture medium can then saturate the selective medium, which then no longer plays its role of selective barrier. The presence of bacteria other than *salmonellae* in the detection system can then constitute a false positive: a positive detection system is detected, whereas the sample is not contaminated with *salmonellae*. In addition, the method as described in that patent application can only be used for motile bacteria.

The present invention proposes to solve all the drawbacks of the state of the art by providing in particular a method for detecting and/or identifying bacteria requiring minimum handling, on the part of the handler, of the culture medium comprising the bacteria, while at the same time allowing a rapid diagnosis directly from the culture medium, that can be readily set up during the bacterial exponential growth phase.

Before proceeding, the following definitions will make it possible to understand the subsequent disclosure of the invention more clearly. "Sample" is intended to mean a dietary sample derived from any type of food, but also a clinical sample derived from a sample of a biological liquid. This sample may thus be liquid or solid, and mention may be made, without implied limitation, of a dietary sample of water, of drinks such as milk, of fruit juice; a clinical sample of blood, plasma, urine or faeces, a dietary sample of yoghurt, meat, eggs, vegetables, mayonnaise or cheese; fish, etc., a dietary sample derived from a food intended for animals, such as in particular a sample derived from animal meals.

The term "first container" is intended to mean any type of container capable of accepting a culture medium, such as in particular a flask, a bottle, a Stomacher® bag, etc. It may be advantageous for this first container to tolerate a variation in pressure, in particular during a variation in temperature. Thus, if the first container is made of a solid material (such as a glass bottle), it is advantageous for this first container to be open, or to be equipped with a valve allowing a pressure variation. When the first container is made of a flexible material, such as in particular a Stomacher® bag, it may be open or closed, since the pressure variation is permitted by the flexibility of the material.

The term "culture medium" is intended to mean a medium comprising all the elements required for the viability and the growth of the cells. Such a culture medium is well known to those skilled in the art, who may readily choose the culture medium most suitable with regard to the bacteria that they desire to detect.

The term "selective medium" is intended to mean a medium that makes it possible to select the bacteria that should react with the system for detecting the bacteria. When it is desired to select, for example, a given bacterium, the selective medium comprises an antibiotic directed against the other bacterial species that may be present in the sample and that it is not desired to detect. Another example would consist in the selective medium comprising a compound that is toxic for certain specific bacteria. A medium that is nutritionally restrictive for certain bacteria can also be used. Such selective media are well known to those skilled in the art, who will choose a suitable selective medium according to the sample and the bacteria that they wish to analyse. This selective medium can be mixed with the culture medium or isolated in a second container comprising the detection system.

The term "second container" is intended to mean any type of container capable of accepting at least one detection system as defined below. This second container is preferably made of a material that is sufficiently rigid for its volume to remain constant when a decrease in temperature is applied inside this second container. This second container may be included in the first container, so that the user has only one device comprising all the means required for detecting and/or identifying bacteria The term "detection system" is intended to mean a system that makes it possible to demonstrate the presence of a given bacterium. Such a system is well known to those skilled in the art and mention may be made, by way of indication, of a detection system comprising a chromogenic or fluorogenic substrate, based on the detection of an immunoprecipitation, an immunochromatography, a pH indicator, a precipitating product, etc. This detection may be direct, i.e. by detection of the bacterium, or indirect, by detection in particular of a metabolite released by said bacterium.

The term "transfer means" is intended to mean any means for transferring a liquid medium included in a first container to a second container. This transfer means and the second container may be independent, or may constitute a single part.

Thus, the invention provides a method for detecting and/or identifying bacteria present in a liquid or solid sample, characterized in that:
  a. the sample that may contain said bacteria is placed in a liquid culture medium, in a first container,
  b. a second container comprising at least one system for detecting said bacteria is provided,
  c. a means of transfer between the first container and the second container is provided,
  d. a temperature T1 is applied inside the second container, then
  e. a temperature T2 is applied inside the second container,
  f. the temperature T1 is higher than the temperature T2 such that a defined volume of culture medium is transferred from the first container to the second container,
  g. the presence or absence of bacteria is determined and/or the bacteria are identified within the detection system.

The bacteria may in particular be, without implied limitation, bacteria of the genus *Staphylococcus, Salmonella, Niesseria, Legionella, Mycobacteria, Campylobacter, Listeria*, etc.

According to a preferred embodiment of the invention the transfer means comprises at least a first opening in the first container and at least a second opening in the second container.

It is clearly understood that the transfer between the first container and the second container does not occur spontaneously. The first opening in the first container should, for example, be located below the second opening in the second container, in order to prevent any spontaneous transfer by gravity. This spontaneous transfer can also be prevented when the transfer means is a non-capillary conduit that prevents any spontaneous transfer between the first container and the second container by simple capillarity. The internal diameter of this conduit may be in particular between 0.1 and 5 mm, preferably between 0.5 and 2 mm.

Preferably, the second container delimits a first volume of air between the second opening and the detection system and/or the transfer means delimits a second volume of air between the first opening and the second opening. If the second container also comprises, between the second opening of the transfer means and the detection system, a selective medium, the volume of air is preferably delimited between the second opening of the transfer means and the selective medium.

According to a preferred embodiment of the invention, the second container and the transfer means are made of materials that are sufficiently rigid to remain at a constant volume when there is a temperature variation. Thus, when the temperature changes from T1 to T2, the first volume of air, and/or the second volume of air, act(s) like an aspirating lung by undergoing a decrease in pressure.

According to a preferred embodiment of the invention, T1 is between 20 and 45° C., and more preferably between 30 and 42° C.; T2 is between 4 and 30° C., preferably between 13 and 18° C.

In step f), the defined volume that is transferred depends in particular on the temperature difference that is applied, and also on the second volume of air. The defined volume that is transferred can be in particular between 100 and 1000 µl, and preferably between 400 and 600 µl. Thus, by way of indication, when the temperature difference (T2−T1) is 22° C., and T1=15° C. and T2=37° C., a volume of 350 µl is transferred from the first container to the second container. It is also possible to carry out steps d) to f) several times, in order to transfer, in several stages, the defined volume for the detection of the bacteria.

In step g), the determination of the presence or absence of bacteria and/or the identification of the bacteria depends on the detection system that is used.

According to a variant of embodiment of the invention, a pre-enrichment step, which consists in increasing the number of bacteria that it is desired to detect, is carried out between step a) and step b). Such a pre-enrichment step is well known to those skilled in the art, who will readily adapt it according to the bacteria that they wish to detect.

According to a particular embodiment of the invention, the second container is included in the first container.

The invention also relates to a method for detecting and/or identifying bacteria present in a liquid or solid sample, characterized in that:
  a. the sample that may contain said bacteria are placed in a liquid culture medium, as defined above, in a first container,
  b. a second container comprising at least one system for detecting said bacteria, as defined above, is provided,
  c. a means of transfer between the first container and the second container, as defined above, is provided,
  d. a temperature T1 is applied inside the first container, then
  e. a temperature T2 is applied inside the first container,
  f. the temperature T1 is lower than the temperature T2 such that a defined volume of culture medium is transferred from the first container to the second container,
  g. the presence or absence of bacteria is determined and/or the bacteria are identified within the detection system.

According to a preferred embodiment of the invention, the second container and the transfer means are made of materials that are sufficiently rigid to remain at a constant volume when there is a temperature variation.

The invention also relates to a device for detecting and/or identifying bacteria in a sample, comprising:
  a second container comprising at least one detection system, and
  at least one means of transfer between a first container and the second container, said transfer means comprising at least a first opening in the first container and at least a second opening in the second container.

According to a preferred embodiment of the invention, the second container delimits a first volume of air between the second opening and the detection system and/or the transfer means delimits a second volume of air between the first opening and the second opening, said first and second volumes of air acting like an aspirating lung when a decrease in temperature is applied in particular within the second container.

According to a preferred embodiment of the invention, the first container and the transfer means are made of materials that are sufficiently rigid so as to remain at a constant volume when there is a temperature variation.

According to a particular embodiment of the invention, the first opening in the first container is positioned lower than the second opening in the second container, in order to prevent in particular any transfer by gravity between the first container and the second container.

According to another embodiment of the invention, the first opening in the first container and the second opening in the second container constitute the same opening.

In this embodiment, the transfer means is then limited to this same opening.

According to a particular embodiment of the invention, the transfer means is a non-capillary conduit, in order to prevent in particular any transfer by simple capillarity between the first container and the second container.

According to a particular embodiment of the invention, the device as defined above also comprises a first container comprising a culture medium. According to a particular embodiment, the second container is included in the first container. Preferably, the first container is a Stomacher® bag. The Stomacher® bag can then comprise a filter, between the culture medium in which the dietary sample is placed and the transfer means, in order to prevent any fragments of the dietary sample from blocking the first opening and preventing transfer of the culture medium from the first container to the second container.

Finally, the invention relates to a kit for detecting and/or identifying bacteria, for implementing the method as defined above.

The attached figures are given by way of explanatory example and are in no way limiting in nature. They will make it possible to understand the invention more clearly.

Figure 1:
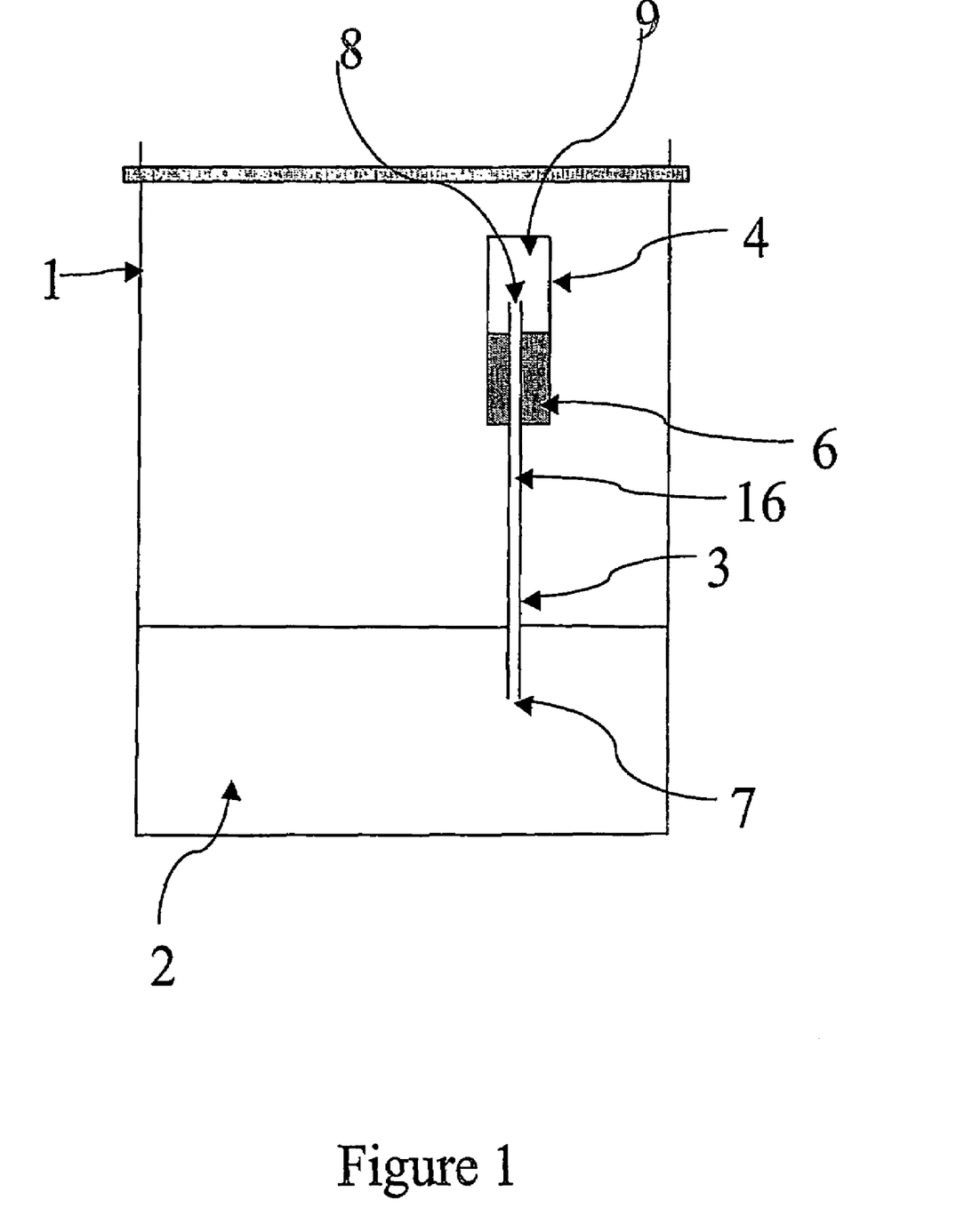

Thus, FIG. 1 shows a first embodiment of the invention, as presented in Example 1. The first container (1) is a Stomacher® bag comprising a culture medium (2) in which the sample that may contain the bacteria that it is desired to detect and/or identify is placed. The second container (4) comprises a detection system (6) which is a selective liquid medium comprising an indicator that forms a precipitate when it is in the presence of the bacterium that it is desired to detect and/or identify. This second container is connected to a transfer means (3), which is immersed in the culture medium (2) comprising the sample. This transfer means comprises a first opening (7) in the first container (1) and a second opening (8) in the second container (4). A first volume of air (9) is delimited between the second opening (8) and the detection system (6). A second volume of air (16) is also delimited within the transfer means (3) between the second opening (8) and the first opening (7).

Figure 2:
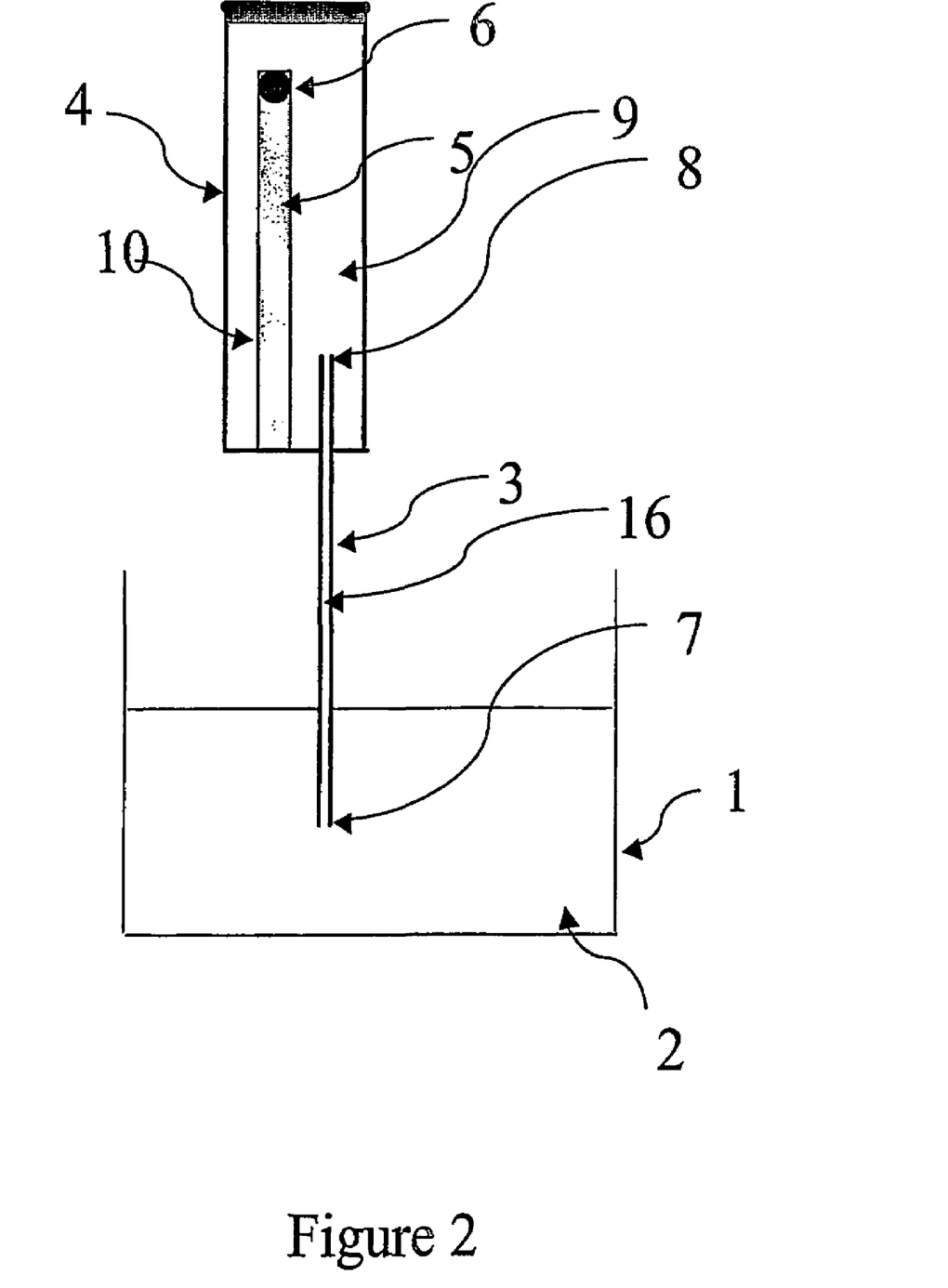

FIG. 2 shows another embodiment of the invention, as presented in Example 2. The first container (1) is an open container comprising a culture medium (2) in which the sample that it is desired to analyse is placed. The transfer means (3) is comparable to that of FIG. 1. The second container (4) comprises a first volume of air (9), as defined in FIG. 1, and a column of cellulose (10) into which a selective medium (5) is soaked. The detection system (6), which is a chromogenic substrate passively immobilized on a disc of sterile paper, is placed at the top of the column of cellulose (10).

Figure 3:
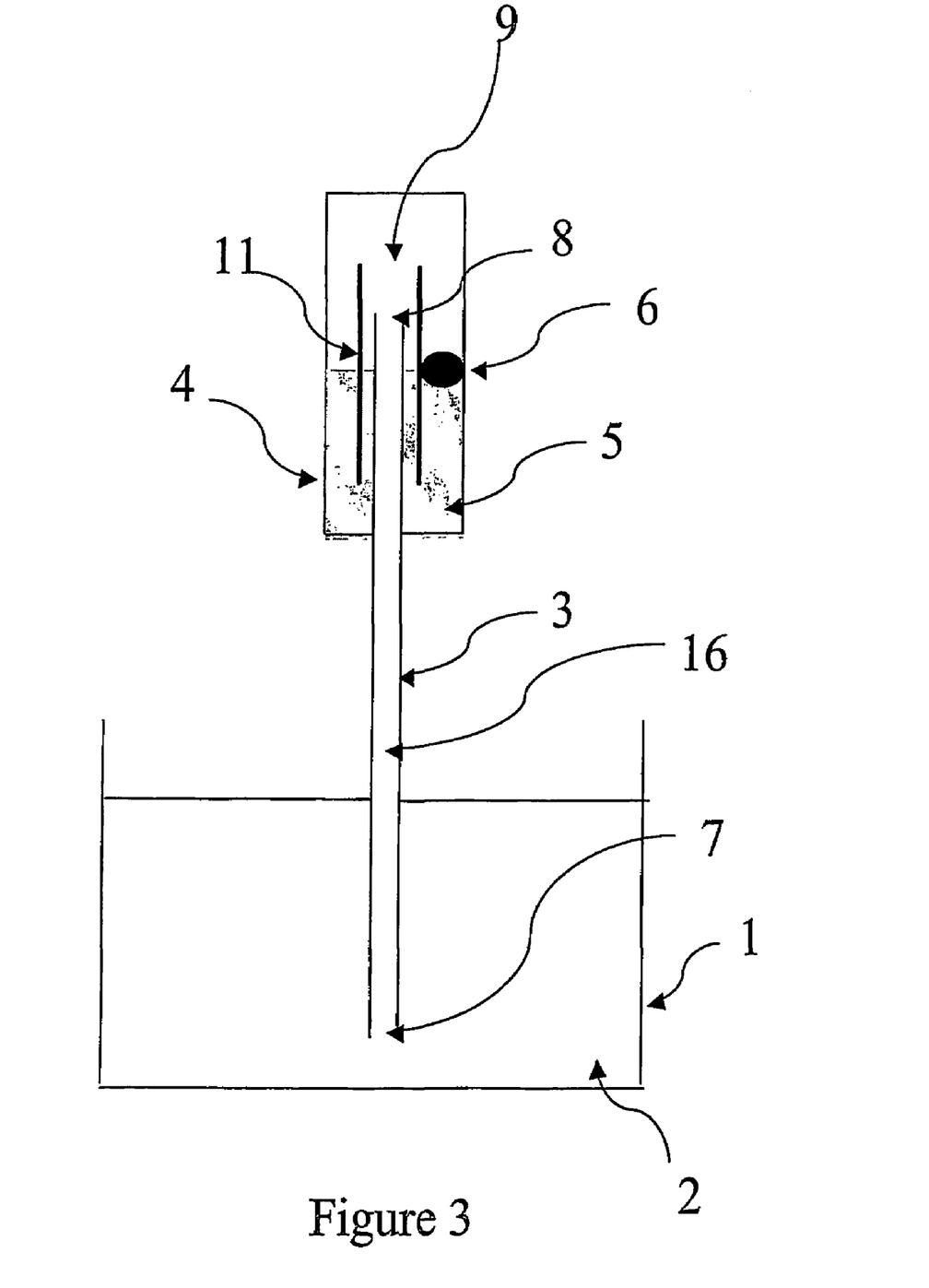

FIG. 3 shows another embodiment of the invention, as presented in Example 3, which finds a preferred application in the detection of motile bacteria The first container (1) is an open container comprising a culture medium (2) in which the sample that it is desired to analyse is placed. The transfer means (3) is comparable to that of FIG. 1. The second container (4) comprises a first volume of air (9) as defined in FIG. 1, a semi-solid selective medium (5), and a detection system (6), which is a chromogenic substrate passively immobilized on a disc of sterile paper. A cylinder (11) forces, after the transfer step, the motile bacteria to migrate through the selective medium before reaching the detection system.

Figure 4:
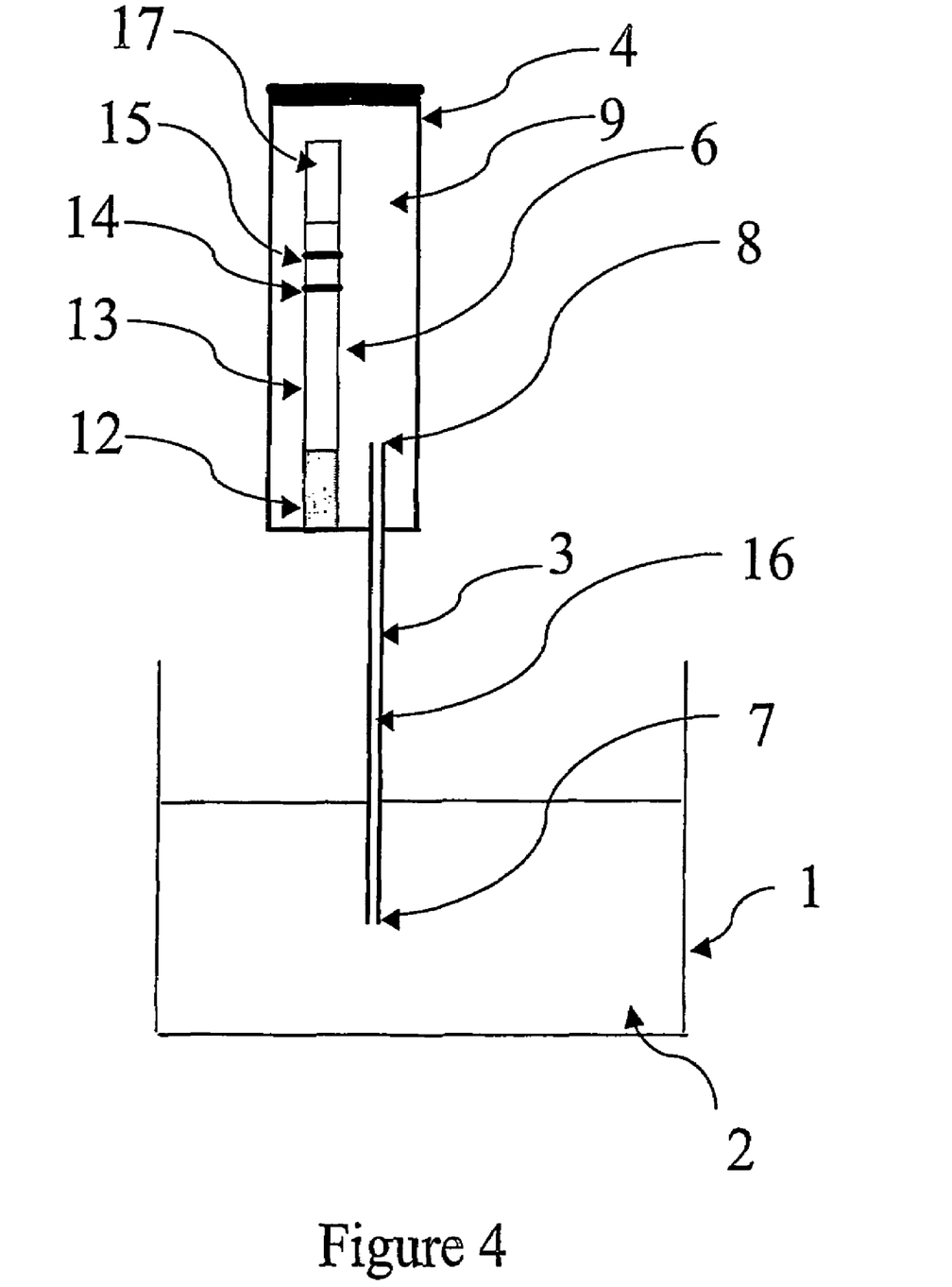

FIG. 4 shows another embodiment of the invention, as presented in Example 4. The first container (1) is an open container comprising a culture medium (2) in which the sample that it is desired to analyse is placed. The transfer means (3) is comparable to that of FIG. 1. The second container (4) comprises a first volume of air (9) as defined in FIG. 1, and a detection system (6) which is an immunochromatography strip, well known to those skilled in the art, comprising a first part (12) containing a labelled anti-bacteria antibody conjugate, and a second part (13), which is a chromatography membrane, on which it is possible to detect a first signal (14) characteristic of the presence of the anti-bacteria antibodies that it is desired to detect, and a second signal (15), characteristic of the presence of a positive control. The absorbent paper (17) allows migration of the bacteria, even if they are not motile.

Figure 5:
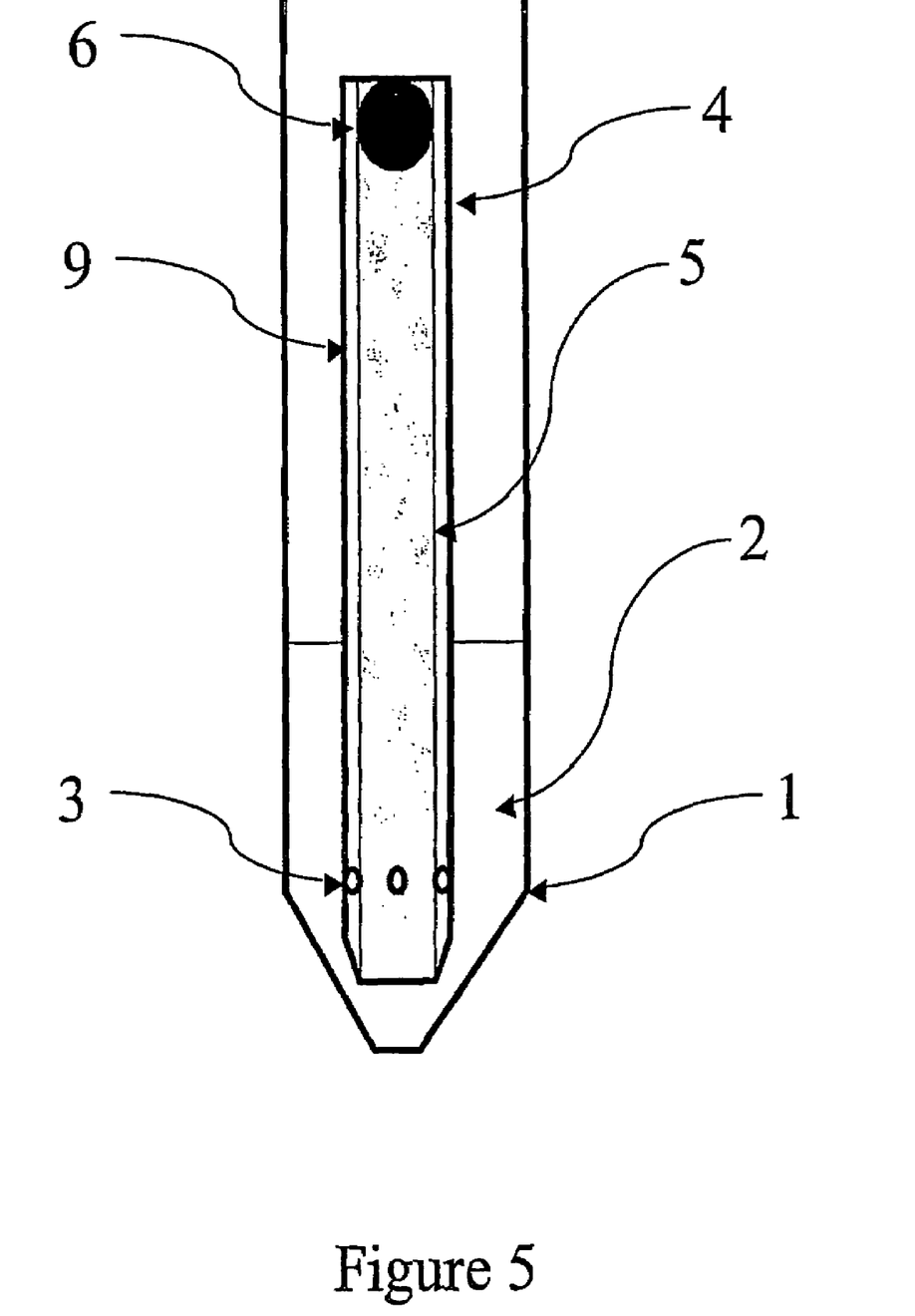

FIG. 5 shows another embodiment of the invention. The first container (1) is a biological analysis tube comprising a culture medium (2) in which the sample that it is desired to analyse is placed. The second container (4) comprises a first volume of air (9) as defined in FIG. 1, and a detection system (6) and a selective medium (5). In this embodiment, the first opening in the first container (1) and the second opening in the second container (4) constitute the same opening: the transfer means (3) is then limited to this same opening. This opening must not allow spontaneous transfer of culture medium between the first and the second container.

The following examples are given by way of illustration, and are in no way limiting in nature. They will make it possible to understand the invention more clearly.

EXAMPLE 1

Detection of *Staphylococcus aureus* on a Liquid Selective Medium Comprising an Indicator A device for detecting and/or identifying bacteria present in a sample as shown in FIG. 1 is used in this example for detecting *Staphylococcus aureus* bacteria. For this, 225 ml of culture medium (2) (peptone water, bioMérieux, ref 42043) are introduced into a first container (1) which is a Stomacher® bag, along with 25 ml of milk, and the mixture is inoculated with $3 \times 10^4$ *Staphylococcus aureus* cells, according to a conventional protocol as known to those skilled in the art. A control test is obtained using culture medium and milk, as presented above, but not inoculated with *Staphylococcus aureus*. The upper part of a 25 ml syringe is used as second container (4) comprising a first volume of air (9) of 13 ml. A selective medium (5) (Qi-Staph®, bioMérieux) is used, and 3 ml of this selective medium are introduced into the second container (4). In this example, the detection system (6) is an indicator compound (potassium tellurite) which allows the appearance of a black precipitate in the presence of *Staphylococcus aureus* bacteria The transfer means (3) used in this example is a conduit, with an internal diameter of 1 mm and a length of 12 cm, 4 cm of which penetrate into the second container (4), as shown in FIG. 1. This transfer means (3) comprises a first opening (7) which is immersed in the culture medium (2), and a second opening (8) which goes into the second container (4). In this example, the second container comprises just one opening, which corresponds to said second opening (8) of the transfer means (3), and, as a result, constitutes a closed chamber with the exception of the opening (8). As shown in FIG. 1, the second container (4) and the transfer means (3) are placed in the Stomacher® bag. This makes it possible to isolate the contaminated culture medium.

The transfer of the culture medium (2) comprising the bacteria between the first container (1) and the second container (4) is obtained by placing the entire device in an incubator at 37° C. for one hour. This incubation allows the pre-enrichment of the culture medium. A more or less long incubation can be carried out according to the contamination of the sample. The inside of the second container (4) is then at a temperature T1=37° C. The entire device is then placed at a temperature of 15° C. for one hour, so that the inside of the second container (4) is at a temperature T2=15° C. This decrease in temperature then induces a decrease in pressure in the second container (4), which allows the transfer of a defined volume of the culture medium (600 µl) from the first container (1) to the second container (4). The entire device is then kept at 37° C. for 18 h, so as to allow the bacteria to metabolize the substrate, inducing the appearance of a precipitate within the detection system (6). It should be noted that, in the second container (4), the level of selective medium (5) does not reach the second opening (8), between the transfer means (3) and the second container (5): during the aspiration, the culture medium (2) comprising the aspirated *Staphylococcus aureus* bacteria is trapped inside the second container (4), and cannot flow back into the first container (1), when the temperature inside the second container (4) is again increased. At the end of this incubation, a precipitate appears within the detection system, confirming the presence of *Staphylococcus aureus* when the culture medium and the milk were inoculated with these bacteria. No precipitate was observed in the control test.

EXAMPLE 2

Detection of *Salmonella typhimurium* Bacteria on a Column of Cellulose

The first container (1) is identical to that described in Example 1, but could be any type of first container. In this example, 225 ml of BPW (peptone water) culture medium (2) in which 25 g of powdered milk (commercially available) are dissolved are inoculated with $3 \times 10^{2^2}$ *Salmonella typhimurium* cells. The second container (4) and the transfer means (3) used in this example are shown in FIG. 2. A control test is carried out as described in Example 1.

For the selective medium (5), 0.5 millilitre of BPW culture medium containing 20 µg of novobiocin are soaked onto a column of cellulose (10), 2 cm long and 0.7 cm in diameter. This column of cellulose (10) is placed inside the second container (4), without however being in contact with the second opening (8) of the transfer means (3). In this example, the second container (4) comprises just one opening, which corresponds to said second opening (8) of the transfer means (3), and, as a result, constitutes a closed chamber with the exception of the opening (8). Deposited at the top of this column of cellulose (10) is the detection system (6), which is a chromogenic substrate, 5-bromo-6-chloro-3-indoxyl octanoate (magenta C8) combined with nitro blue tetrazolium (Sigma, N6639), passively immobilized on a disc of sterile paper 5 mm in diameter (Whatman 3 Chr, ref 3030917). The transfer of the culture medium (2) comprising the bacteria between the first container (1) and the second container (4) is carried out as described in Example 1, by placing the entire device at 37° C. for 1 hour, and then at 15° C. for one hour. At the end of the transfer, the bacteria in contact with the column of cellulose diffuse up to the top of the column, to the detection system where they metabolize the substrate, so as to form a black precipitate. Positive results are observed after 15 h. The results were negative in the control test.

EXAMPLE 3

Detection of Motile *Salmonella typhimurium* Bacteria on a Semi-solid Selective Medium The first container (1) is that described in Example 1, but can be any type of first container. In this example, 225 ml of BPW (peptone water) culture medium (2), in which 25 g of powdered milk (commercially available) are dissolved, are inoculated with $3 \times 10^4$ *Salmonella typhimurium* cells. The second container (4) and the transfer means (3) used in this example are shown in FIG. 3. A control test is carried out as described in Example 1.

3 ml of semi-solid medium (API M-medium®, bioMérieux, ref 50120) are placed inside the second container (4) and used as selective medium (5) comprising 40 µg/ml of novobiocin, without the level of selective medium (5) reaching the second opening (8) between the transfer means (3) and the second container (5). The second opening (8) and the detection system (6) are separated by a cylinder (11) as shown in FIG. 3, forcing the bacteria to migrate through the selective medium (5), which means that only the resistant and motile bacteria reach the detection system (6). The detection system (6) is a chromogenic substrate as described in Example 2.

The transfer of *salmonellae* from the first container to the second container is carried out, in a manner comparable to Example 1, by placing the entire device at 37° C. for 1 hour, and then at 15° C. for one hour.

At the end of the transfer step, by maintaining the entire device at 37° C. for 16 h, a defined volume of culture medium (150 µl) comprising the motile bacteria is in contact with the selective medium (5), and the bacteria migrate through it, to the detection system (6). At the end of this incubation, the black coloration of the disc confirms the presence of *salmonellae*, initially present in the culture medium. No coloration was observed in the control test.

EXAMPLE 4

Detection of *Listeria monocytogenes* Bacteria by Immunochromatography

The first container (1) is that described in Example 1, but can be any type of first container. In this example, 250 ml of culture medium (2) (trypcase soy broth, bioMérieux, ref 44011; 6% of yeast) are inoculated with $3 \times 10^7$ cfu/ml of *Listeria monocytogenes* 4b. The second container (4) and the transfer means (3) used in this example are shown in FIG. 4. A control test is carried out in a comparable manner, but without bacterial inoculation.

The detection system (6), which is an immunochromatographic strip well known to those skilled in the art, is placed inside the second container (4). A control test is carried out as described in Example 1.

The transfer of *Listeria monocytogenes* from the first container (1) to the second container (4) is carried out by incubation of the entire device at a temperature T1=30° C. for one hour, and then at a temperature T2=15° C. for 45 min. At the end of the transfer, it is possible to detect a first signal (14), characteristic of the presence of a protein present in the flagellum of *L. monocytogenes*, by reaction with specific antibodies, and a second signal (15), characteristic of the presence of a positive control and obtained using an antibody against IgG from mouse. In the control test, only the second signal could be observed.

REFERENCES

1. First container
2. Culture medium comprising the sample
3. Transfer means
4. Second container
5. Selective medium
6. Detection system
7. First opening
8. Second opening
9. First volume of air
10. Column of cellulose
11. Cylinder
12. First part
13. Second part
14. First signal
15. Second signal
16. Second volume of air
17. Absorbent paper

The invention claimed is:

1. A method for detecting and/or identifying bacteria present in a liquid or solid sample, wherein:
   a. the sample that may contain said bacteria is placed in a liquid culture medium, in a first container;
   b. a second container comprising at least one system for detecting said bacteria is provided separate from said first container;
   c. a means of transfer between the first container and the second container is provided, said means of transfer comprising at least a first opening in the first container and at least a second opening in the second container, such that the second container delimits a first volume of air between the second opening of the transfer means and the at least one system for detecting said bacteria and/or delimits a second volume of air between the first opening and the second opening;
   d. a temperature T1 is applied inside the second container; then
   e. a temperature T2 is applied inside the second container;
   f. the temperatures T1 and T2 are applied inside the second container at an exponential growth phase of the bacteria;
   g. the temperature T1 is higher than the temperature T2;
   h. the temperatures T1 and T2 are applied inside the second container such that a predetermined volume of culture medium with bacteria is transferred from the first container to the second container;
   i. the temperatures T1 and T2 are maintained such that the bacteria remain viable; and
   j. the presence or absence of bacteria is determined and/or the bacteria are identified with the at least one system for detecting said bacteria in said second container.

2. The method according to claim 1, wherein T1 is between 25 and 45° C.

3. The method according to claim 1, wherein T2 is between 4 and 24° C.

4. A kit for detecting and/or identifying bacteria by means of implementing the method according to claim 1.

5. The method according to claim 2, wherein T1 is between 30 and 42° C.

6. The method according to claim 3, wherein T2 is between 13 and 18° C.

* * * * *